US00PP18070P2

(12) United States Plant Patent
Hofmann

(10) Patent No.: US PP18,070 P2
(45) Date of Patent: Sep. 25, 2007

(54) ***GERANIUM* PLANT NAMED 'TIKSCARL'**

(50) Latin Name: *Pelargonium×hortorum*
Varietal Denomination: Tikscarl

(75) Inventor: Christa Hofmann, Radeburg (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 11/358,919

(22) Filed: Feb. 17, 2006

(51) Int. Cl.
*A01H 5/00* (2006.01)

(52) U.S. Cl. ..... Plt./325

(58) Field of Classification Search ..... Plt./325
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of Zonal *Geranium* plant named 'Tikscarl', characterized by its vigorous and spreading growth habit; freely basal branching and flowering habit; light red-colored non-persistent flowers; and good garden performance.

1 Drawing Sheet

Botanical designation: *Pelargonium×hortorum.*
Cultivar denomination: 'Tikscarl'.

BACKGROUND OF THE INVENTION

The present invention relates to a new and distinct cultivar of Zonal *Geranium* plant, botanically known as *Pelargonium×hortorum,* and hereinafter referred to by the name 'Tikscarl'.

The new Zonal *Geranium* is a product of a planned breeding program conducted by the Inventor in Dresden, Germany. The objective of the breeding program was to develop new vigorous Zonal Geraniums with attractive flower coloration.

The new Zonal *Geranium* originated from a cross-pollination made by the Inventor in 1996 of two unnamed proprietary selections of *Pelargonium×hortorum,* not patented. The cultivar Tikscarl was discovered and selected by the Inventor as a flowering plant within the progeny from the stated cross-pollination in a controlled environment in Dresden, Germany in 1997.

Asexual reproduction of the new cultivar by terminal cuttings in a controlled environment in Dresden, Germany since 1998 has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Tikscarl'. These characteristics in combination distinguish 'Tikscarl' as a new cultivar and distinguish it from other known Zonal *Geranium* cultivars:

1. Spreading and vigorous growth habit.
2. Freely basal branching and flowering habit.
3. Light red-colored non-persistent flowers.
4. Good garden performance.

Plants of the new Zonal *Geranium* differ primarily from plants of the parent selections in flower color and flower form.

Plants of the new Zonal *Geranium* can be compared to plants of the cultivar Tikorg, not patented. In side-by-side comparisons conducted in Dresden, Germany, plants of the new Zonal *Geranium* differed from plants of the cultivar Tikorg in the following characteristics:

1. Leaves of plants of the new Zonal *Geranium* had a less distinct zonation pattern than leaves of plants of the cultivar Tikorg.
2. Plants of the new Zonal *Geranium* and the cultivar Tikorg differed in flower color as plants of the cultivar Tikorg had dull orange-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a close-up view of typical leaves and flowers of 'Tikscarl'.

DETAILED BOTANICAL DESCRIPTION

Plants of the cultivar Tikscarl have not been observed under all possible environmental conditions. The phenotype may vary somewhat with variations in environment, such as temperature and light intensity, without, however, any variance in genotype.

The aforementioned photograph, following observations and averaged measurements describe plants grown during the spring in containers in Dresden, Germany, and under commercial practice in a glass-covered greenhouse with day temperatures about 18° C., night temperatures about 16° C. and light levels ranging from 15 to 100 kilolux. Plants used for the photograph and the description were about five months old. In the following description, color references are made to The Royal Horticultural Society Colour Chart, 1995 Edition, except where general terms of ordinary dictionary significance are used.

Botanical classification: *Pelargonium×hortorum* cultivar Tikscarl.

Parentage:

*Female, or seed, parent.*—Unnamed proprietary selection of *Pelargonium×hortorum,* not patented.

*Male, or pollen, parent.*—Unnamed proprietary selection of *Pelargonium×hortorum,* not patented.

Propagation:

*Type cutting.*—Terminal cuttings.

*Time to initiate roots, summer.*—About 18 days at 22° C.

*Time to initiate roots, winter.*—About 22 days at 22° C.

*Time to produce a rooted young plant, summer.*—About 25 days at 22° C.

*Time to produce a rooted young plant, winter.*—About 30 days at 22° C.

*Root description.*—Fine, fibrous; white in color.

*Rooting habit.*—Freely branching, dense.

Plant description:

*General appearance.*—Spreading and vigorous growth habit; uniform; densely foliated. If supported, can be grown on a pillar or can be grown as a ground cover.

*Growth and branching habit.*—Vigorous growth habit. Freely basal branching habit with about 15 lateral branches per plant; pinching is not required.

*Plant height, to top of umbels.*—About 80 cm.

*Plants height, to top of foliar plane.*—About 70 cm.

*Plant width.*—About 40 cm.

*Lateral branches.*—Length: About 15 cm. Diameter: About 7 mm. Internode length: About 3 cm. Texture: Pubescent. Color: 146A.

*Foliage description.*—Arrangement: Opposite; simple. Length: About 4 cm to 5 cm. Width: About 7 cm to 8 cm. Shape: Reniform. Apex: Rounded. Base: Cordate; open to closed. Margin: Bicrenate. Venation pattern: Palmate. Texture, upper surface: Pubescent. Texture, lower surface: Smooth. Color: Developing and fully expanded foliage, upper surface: 147A; venation, 147B. Developing and fully expanded foliage, lower surface: 147B; venation, 147B. Zonation pattern: Intensity: More distinct on developing leaves. Location of zone from margin: About 1 cm. Width: About 1 cm. Color: Darker than 147A. Petiole: Length: About 6 cm to 7 cm. Diameter: About 2 mm. Texture, upper and lower surfaces: Pubescent. Color, upper and lower surfaces: 138A.

Flower description:

*Flower arrangement.*—Light red-colored flowers; single rotate flowers arranged in rounded hemispherical umbels arising from apical leaf axils. Umbels displayed upright above the foliage on strong peduncles. Flowers face upright to outwardly; flowers mostly flat and uniform. Flowers persistent. Flowers not fragrant.

*Quantity of flowers.*—Freely flowering habit; about 20 flower buds and open flowers per umbel.

*Flowering season.*—Year-round under greenhouse conditions. In the garden in Dresden, Germany, flowering is continuous from May until October.

*Flower longevity.*—Individual flowers last about ten days.

*Umbel height.*—About 6 cm.

*Umbel diameter.*—About 11 cm.

*Flower diameter.*—About 4 cm to 4.5 cm.

*Flower depth* (*height*).—About 1 cm.

*Flower buds.*—Length: About 9 mm to 12 mm. Diameter: About 4 mm to 6 mm. Shape: Elliptic; elongated. Color: 138A.

*Petals.*—Quantity per flower: About five. Length: About 2.5 cm. Width: About 2.2 cm. Shape: Roughly obovate. Apex: Rounded to slightly cordate. Base: Attenuate. Margin: Entire. Texture, upper and lower surfaces: Smooth, glabrous; velvety. Color: When opening and fully opened, upper surface: 40A; venation, 42A; towards the base, close to 155D. When opening and fully opened, lower surface: 44C; venation, 41B; towards the base, close to 155D.

*Sepals.*—Quantity per flower: Five, arranged in a single whorl. Length: About 1 cm. Width: About 4 mm. Shape: Elliptic. Apex: Acute. Base: Attenuate. Margin: Entire. Texture, upper and lower surfaces: Pubescent. Color, upper surface: 138B. Color, lower surface: 138A.

*Peduncle* (*umbel stem*).—Length: About 15 cm to 20 cm. Diameter: About 3 mm. Strength: Strong. Aspect: Upright. Texture: Pubescent. Color: 144A overlain with close to 178A.

*Pedicel* (*individual flower stem*).—Length: About 3.5 cm to 4 cm. Diameter: About 2 mm. Strength: Moderately strong; flexible. Texture: Pubescent. Color: 144C overlain with 178A.

*Reproductive organs.*—Androecium: Stamen quantity per flower: About five to seven. Anther length: About 1 mm to 2 mm. Anther shape: Oblong. Anther color: 169A. Pollen amount: Abundant. Pollen color: 169A. Gynoecium: Pistil quantity per flower: One. Pistil length: About 7 mm. Stigma shape: Five-parted. Stigma color: 46A. Style length: About 2 mm to 3 mm. Style color: 150D. Ovary color: 142C. Seeds: Seed production has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 0° C. to about 35° C. and have demonstrated good garden performance.

It is claimed:

1. A new and distinct cultivar of Zonal *Geranium* plant named 'Tikscarl', as herein illustrated and described.

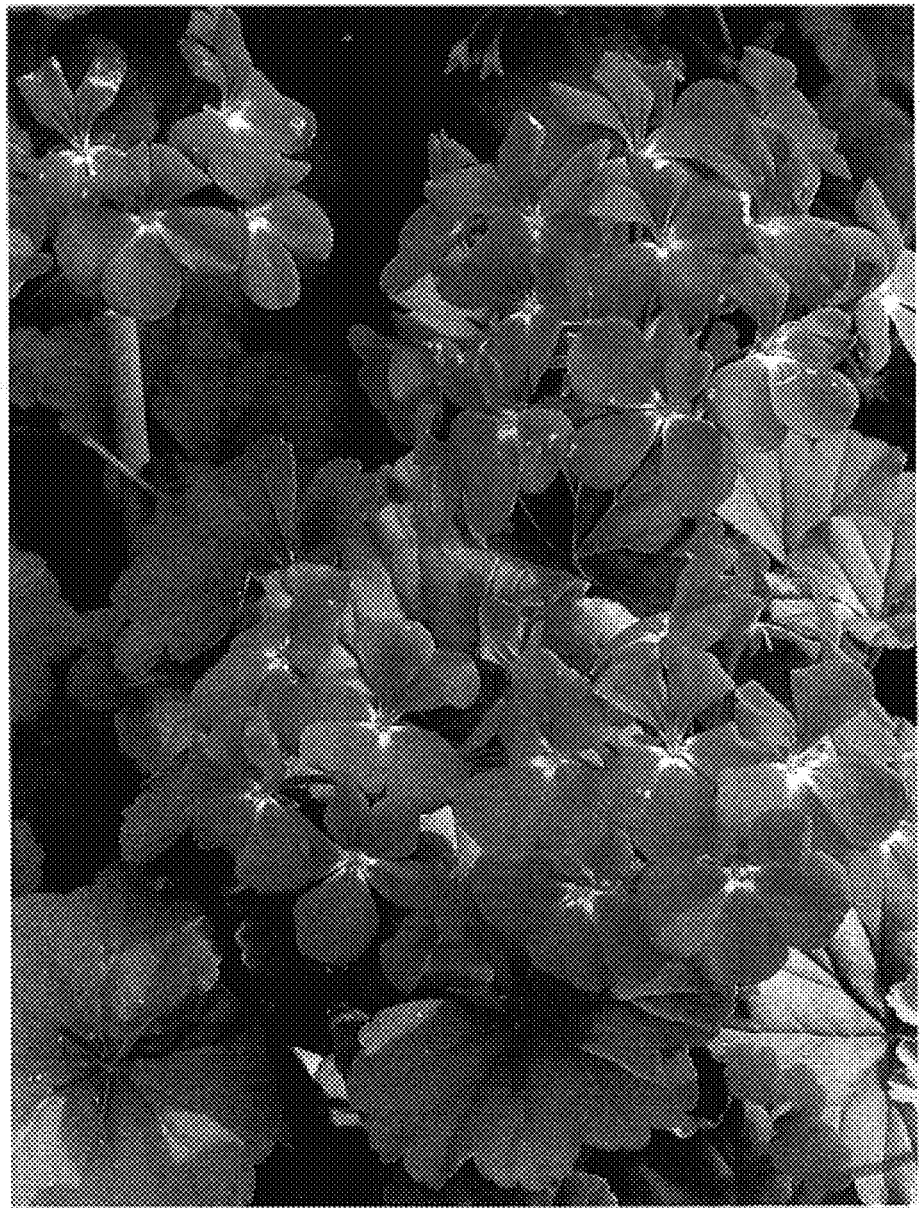

* * * * *